United States Patent
Koziak et al.

(10) Patent No.: US 11,452,728 B2
(45) Date of Patent: Sep. 27, 2022

(54) 7-AMINOCEPHALOSPORANIC ACID DERIVATIVE AS INHIBITOR OF IL15 AND IL-2 ACTIVITY

(71) Applicant: Warszawski Uniwersytet Medyczny, Warsaw (PL)

(72) Inventors: Katarzyna Koziak, Warsaw (PL); Barbara Zyzynska-Granica, Warsaw (PL); Slawomir Filipek, Warsaw (PL); Szymon Niewieczerzal, Warsaw (PL); Bartosz Trzaskowski, Warsaw (PL); Oliwia Zegrocka-Stendel, Lomianki (PL); Malgorzata Dutkiewicz, Warsaw (PL); Piotr Krzeczynski, Warsaw (PL); Elzbieta Kaczmarek, Warsaw (PL); Magdalena Winiarska, Warsaw (PL)

(73) Assignee: Bio Research Project PSA, Warsaw (PL)

(*) Notice: Subject to any disclaimer, the term of this patent is extended or adjusted under 35 U.S.C. 154(b) by 0 days.

(21) Appl. No.: 15/661,586

(22) Filed: Jul. 27, 2017

(65) Prior Publication Data
US 2017/0319593 A1 Nov. 9, 2017

Related U.S. Application Data

(62) Division of application No. 15/026,125, filed as application No. PCT/IB2014/001940 on Sep. 29, 2014, now abandoned.

(30) Foreign Application Priority Data

Sep. 30, 2013 (PL) .................................. 405506

(51) Int. Cl.
*A61K 31/546* (2006.01)
*A61K 9/00* (2006.01)

(52) U.S. Cl.
CPC .......... *A61K 31/546* (2013.01); *A61K 9/0019* (2013.01)

(58) Field of Classification Search
CPC ..... A61K 31/546; A61K 9/0019; A61P 17/06; A61P 19/02; A61P 1/00; A61P 29/00; A61P 35/00; A61P 35/02; A61P 37/06
See application file for complete search history.

(56) References Cited

U.S. PATENT DOCUMENTS

2003/0236265 A1* 12/2003 Sayada ................ A61K 31/496
514/252.13
2007/0202077 A1 8/2007 Brodsky et al.

FOREIGN PATENT DOCUMENTS

CN 1247057 A * 3/2000
JP 2007131535 A 5/2007
WO 2007065167 A1 6/2007

OTHER PUBLICATIONS

Grove, Biological & Biomedical Sciences, Issue 1, Jun. 2001.*
Pearce, Everyday Health, Jan. 21, 2008.*
Cefazolin product label, Jan. 12, 2011 as captured by Wayback machine.*
S et al., Dermatology. 2012;225(1):54-61, Incyte Corporation, J Am Acad Dermatol, Mar. 2009 (Year: 2009).*
ML. et al., Int J Immunopharmacol. 1991;13(8):1099-107 (Year: 1991).*
Marcus et al, Dermatol Reports. Aug. 3, 2011; 3(2): e14. (Year: 2011).*
Villeda-Gabriel et al., Arch Med Res. Summer 1998;29(2):143-8, (Year: 1998).*
Contemporary Pediatrics, Relevant Topics, Streptococcal infection as trigger for psoriasis, Mar. 1, 2011, (Year: 2011).*
Kaur et al., Comparative Study, Dermatology 2012;225(1):54-61, Epubl Aug. 9, 2012, (Year: 2012).*
Broatas et al., Anais Brasileiros de Dermatologia, Sep./Oct. 2012. (Year: 2012).*
Dupire et al., Cochrane Database of Systematic Reviews 2019, Issue 3. Art. No: CD011571 (Year: 2019).*
Grace K. Kim, Do, et al., "Drug-Provoked Psoriasis: Is It Drug Induced or Drug Aggrravated?, Understanding Pathophysiology and Clinical Relevance," Jan. 2010, vol. 3, No. 1, 7 pages.
Giulio Kleiner, et al., Research Article "Cytokine Levels in the Serum of Healthy Subjects," Mediators of Inflammation, vol. 2013, Article ID 434010, 7 pages.
Chiodini et al., "In Vitro Antimicrobial Susceptibility of a *Mycobacterium* sp. Isolated From Patients With Crohn's Disease", Antimicrobial Agents and Chemotherapy, American Society for Microbiology, vol. 26, No. 6, Dec. 1, 1984, pp. 930-932.
Öncül et al., "Serum Interleukin 2 Levels in Patients With Rheumatoid Arthritis and Correlation With Insulin Sensitivity", Journal of International Medical Research, vol. 30, No. 4, Aug. 1, 2002, pp. 386-390.
Reddy et al., "Relapses of Inflammatory Bowel Disease During Pregnancy: In-Hospital Management and Birth Outcomes", Am J Gastroenterol. May 2008; 103(5):1203-9.
Healthline Editorial Team, "Rheumatoid Arthritis Prevention", http://www.healthline.com/health/rheumatoid-arthritis-prevention. Overview, Medically Reviewed by Brenda B. Spriggs, MD on Sep. 4, 2014.
Samson Medical Technologies, L.L.C., "Cefazolin for Injection, USP", Pharmacy Bulk Package—Not for Direct Infusion, https://dailymed.nlm.nih.gov/dailymed/archives/fdaDrugInfo.cfm?archiveid=27606, retrieved Apr. 12, 2017, 18 pgs.
C. M. Owen et al, "A systematic review of antistreptococcal interventions for guttate and chronic plaque psoriasis", British Journal of Dermatology, vol. 145, 2001, pp. 886-890 (5 pages).
B. Dogan et al, "Antistreptococcal treatment of guttate psoriasis: a controlled study", International Journal of Dermatology, vol. 47, 2008, pp. 950-952 (3 pages).

(Continued)

*Primary Examiner* — Jean P Cornet
(74) *Attorney, Agent, or Firm* — Osha Bergman Watanabe & Burton LLP (57) ABSTRACT

The invention relates to a 7-aminocephalosporanic acid derivative, Cefazolin, for use as an inhibitor of IL-15 and IL-2 receptors in the prevention and treatment of diseases related to IL-15 and IL-2 overproduction.

13 Claims, 3 Drawing Sheets

(56) References Cited

OTHER PUBLICATIONS

T. Bergner et al, "Psoriasis and tetracyclines", Journal of the American Academy of Dermatology, pp. 770 (1 page).

L. Dogra et al, "A Controlled Trial of Oral Rifampin in Chronic Plaque Psoriasis", British Journal of Medicine & Medical Research, 4(17), 2014, pp. 3248-3254 (7 pages).

K. Sugiura et al, "Generalized Pustular Psoriasis Triggered by Amoxicillin in Monozygotic Twins with Compound Heterozygous IL36RN Mutations: Comment on the Article by Navarini et al.", Journal of Investigative Dermatology, vol. 134, 2014, pp. 578-579 (2 pages).

* cited by examiner

7-AMINOCEPHALOSPORANIC ACID DERIVATIVE AS INHIBITOR OF IL15 AND IL-2 ACTIVITY

The present amendment is a divisional application of U.S. Ser. No. 15/026,125 filed Mar. 30, 2016 currently pending which is a United States National Stage Entry from PCT/IB2014/001940 filed Sep. 29, 2014. PCT/IB2014/001940 claims priority to Polish application Number P.405506 filed Sep. 30, 2013. The present invention relates to 7-aminocephalosporanic acid derivative for the use in the prevention and treatment of the diseases related to overproduction of interleukin 15 and interleukin 2, such as, rheumatoid arthritis, psoriasis, inflammatory bowel disease, sarcoidosis, T-cell leukemias or transplant rejection.

BACKGROUND

Interleukin 15 (IL-15) is the cytokine exerting pleiotropic activity towards immune system cells as well as other cell types. IL-15 exhibits broad spectrum bioactivity, therefore it is placed at the top of the pro-inflammatory cytokines cascade. The impairment of the mechanisms regulating the expression of IL-15 results in the overproduction of this cytokine and contributes directly to the development of such pathologies as inflammatory processes, autoimmune diseases, infections and neoplastic changes. IL-15 is considered a crucial cytokine in the etiology of rheumatoid arthritis (McInnes I. B. et al., Nat. Med. 2, 175-82 (1996; McInnes•I. B. et al., Nat. Med. 3, 189-95 (1007); McInnes I. B. et al., Immunol Today 19, 75-9 (1998), psoriasis (Villadsen L. S. et al., J. Clin. Invest. 112, 1571-80 (2003), inflammatory bowel disease (Kirman I, Nielsen O. H., Am. J. Gastroenterol 91, 1789-1794 (1996); Sakai T. et al., Gastroenterology 114, 1237-1243 (1998)), sarcoidosis (Agostini C. T. L. et al., J. Immunol. 157, 910-8 (1996)) and T-cell leukemias (Dobbeling U. et al., Blood 92, 252-8 (1998)). Much attention is given to IL-15, on account of participation of this cytokine in transplant rejection (Baan C. C. et al., Transplant Proc. 31, 2726-8 (1999); Lewis E. C. et al., Cytokine 34, 106-13 (2006); Shi R. et al., Transpl. Immunol. 12, 103-8 (2004); Ferrari-Lacraz S. et al., Transplantation 82, 1510-7 (2006); Zheng X. X. et al., Transplantation 81, 109-16 (2006)).

Significant involvement of IL-15 in the development of the pathogeneses of the aforementioned afflictions suggests that targeting this cytokine signaling pathway can reduce or eliminate the occurrence of IL-15-related disorders. This strategy has been proved lately by a number of biological assays. Reduction of IL-15-mediated biological responses, using soluble IL-15Ra receptor (Liew F. Y., McInnes I. B., Ann. Rheum. Dis. 61 Supl. 2, ii100-2 (2002); Ruchatz H. et al., J Immunol. 160, 5664-60 (1998); Smith X. G. et al., J. Immunol. 165, 3444-50 (2000); Wei X et al., J. Immunol. 167, 277-82 (2001)), antibodies inhibiting IL-2/IL-15Rβ receptor (Morris J. C., Proc. Natl. Acad. Sci. USA 103, 401-6 (2001); Tinubu S. A. et al., J. Immunol. 153, 4330-8 (1994), antibodies inhibiting IL-15 (Villadsen L. S. et al. J. Clin. Invest. 112, 1571-80 (2003) or modified IL-15 molecule of competitive antagonist activity (Ferrari-Lacraz S. et al., J. Immunol. 173, 5818-26 (2004); Kim Y. S. et al., J. Immunol. 160, 5742-8 (1998)) always resulted in the alleviation of the disease symptoms. The experimental therapies demonstrated decreased occurrence of collagen-induced rheumatoid arthritis incidence in mice (Ruchatz H. et, al., J Immunol. 160, 5664-60 (1998); Ferrari-Lacraz S. et al., J. Immunol. 173, 5818-26 (2004); Kim Y. S. et al., J. Immunol. 160, 5742-8 (1998)) and primates (Liew F. Y., Mcinnes 1.8., Ann. Rheum. Dis. 61 Supl. 2, ii100-2 (2002)), attenuation of psoriasis symptoms in the mice model of the disease (Villadsen L. S. et al., J. Clin. Invest. 112, 1571-80 (2003)), reduction of carrageenan-induced inflammation in mice (Wei X et al., J. Immunol. 167, 277-82 (2001)) and, also in mice, prolonged survival of heart allotransplants (Smith X. S. et al., J. Immunol. 165, 3444-50 (2000); Tinubu S. A. et al., J. Immunol. 153, 4330-8 (1994) and islets of Langerhans (Ferrari-Lacraz S. et al., J. Immunol. 173, 5818-26 (2004)). Currently adopted strategies based on inhibiting IL-15 seem to be effective, but none of them has been approved for clinical use so far. The most advanced and promising, from the medical application point of view, are the trials aimed at the inhibition of IL-15 activity by anti-IL-15 human antibodies (HuMax-IL 15, AMG-714) (Baslund B. et al., Arthritis Rheum 52, 2686-92 (2005)). However, the matter of serious concern is the effect of 'reverse signaling' (Budagian V. et al., J. Bioi. Chern. (2004)). It is assumed that the antibody HuMax-IL15 and IL-15 complex can itself induce a cell response, thus limiting the therapeutic effectiveness of this antibody directed toward IL-15 neutralization (Budagian V. et al. Cytokine Growth Factor Rev. 17, 259-80 (2006).

In addition, our unpublished results demonstrate significant angiogenic activity of IL-15. The participation of IL-15 in angiogenesis in vivo has already been reported (Angiolllo A. L. et al., Biochem. Biophys. Res. Commun. 233, 231-7 (1997); Kuniyasu H. et al., Pathobiology 69, 86-95 (2001)}, but our recent outcomes have also shown IL-15-induced proliferation and migration of endothelial cells. The identification of another angiogenic factor was not surprising, because its presence had already been detected in rheumatoid arthritis, where the impaired mechanism of angiogenesis is considered to be the main pathogenesis of this illness.

Rheumatoid arthritis (RA) is the most common systemic disease of connective tissue, which affects on average about 1% of the world's population. Recent estimates have shown higher prevalence in women than in men (3:1). The highest prevalence of RA has been reported in the 30-60 age range. It is assumed, about 30% of people afflicted with RA suffer from severe symptoms, which are the leading causes of disabilities within several years. The average life span of people suffering from RA is about 10 years shorter, according to the statistical data. It is thought that the onset of RA results from the complex combination of many factors, such as genetic predisposition, impaired innate and acquired immune response as well as environmental components. Pharmacological treatment of RA, currently available on the medical market, does not remove the cause of the disease. Non-steroidal anti-inflammatory drugs (NSAIDs) are medications, which help managing chronic pain (analgesic effect) and reduce the inflammation, when used over a period of time. They suppress the symptoms of the disease, but do not stop the progress of the illness.

Among the disease-modifying antirheumatic drugs (DMARDs), the first line treatment in RA is methotrexate. The other synthetic DMARDs are leflunomide, sulfasalazine, hydroxychloroquine, D-penicillamine, gold salts, azathioprine, cyclosporine and cyclophosphamide. However, even in patients responding to the treatment, the disease progresses and diminished medical efficacy is observed after long term treatment.

The other class of DMARDs are the biologic medical products. Among the drugs available on the pharmaceutical market, the inhibitors of tumor necrosis factor (TNF) are to be mentioned.

infliximab (chimeric anti-TNF monoclonal antibody);

etanercept (fusion protein, consisting of the extracellular receptor domain p75 for TNF and the Fc fragment of the human antibody IgG1);

adalimumab (human anti-TNF monoclonal antibody), as well as the inhibitors of other proteins:

anakinra, IL-1 receptor antagonist;

abatacept, fusion protein composed of the Fc region of the immunoglobulin IgG1 fused to the extracellular domain of CTLA-4. By binding B7-1 and B7-2 co-stimulating molecules located on the antigen-presenting cells it inhibits the co-stimulatory signal transduction by CD28 on T cells;

rituximab, chimeric monoclonal antibody against the protein CD20 primarily found on the surface of mature B cells acting by eliminating B cells;

tocilizumab, humanized monoclonal antibody against interleukin 6 receptor, has been approved for the European pharmaceutical market as the first IL-6 inhibitor.

Positive results of phase II clinical trials carried out by Amgen company with AMG-714 (previously HuMax-IL15)—human monoclonal antibody that targets IL-15, were disclosed in 2004 (McInnes, I., et al.). However, to date there is no available information about the phase III clinical trials.

The introduction of the biologic medical products into rheumatoid arthritis therapy is considered big progress in the RA treatment, but these biologics (usually used in a combination with methotrexate of cytostatic and immunosuppressive properties) are only effective in limiting the disease symptoms and delaying joint degradation in about 30% of treated patients.

Due to the limited therapeutic effects and high production costs of currently available biologic medical products, the demand for an efficacious anti-RA drug of new generation still remains valid. Ongoing research is aimed at discovering new molecular mechanisms for targeted therapies.

Peptides of modified sequences mimicking IL-15 (revealed, among others, in WO2006/029578 and WO 2010/037351) have also been proposed as potential pharmaceuticals in the rheumatoid arthritis treatment. These peptides are supposed to bind to the receptor IL-15Rα subunit, which should result in the inhibition of T cells proliferation, diminished TNF-α induction as well as expression of IL-8 and IL-6. To date the efficacy of these new compounds has not been proved in clinical studies.

There are other cytokines, which participate in the pathogenesis of inflammatory diseases, induced by interleukin 15 overproduction.

In the complex network of the immune mediators, interleukin 2 (IL-2) is regarded the pivotal cytokine controlling proliferation and differentiation of the immune cells. IL-2 activates, among others, proliferation and differentiation of T lymphocytes, differentiation of T lymphocytes towards cytotoxic T lymphocytes, growth and differentiation of B lymphocytes, activation and proliferation of NK cell, and macrophages activation. Under physiological conditions IL-2 is not detected in a blood serum. Due to its contribution to the activation and stimulation of the effector function of the immune cells, this cytokine is considered one of the chief inflammatory mediators in the autoimmune diseases. IL-2 is released predominantly by activated T helper lymphocytes (CD4+), it is also secreted by CD8+T lymphocytes, dendritic cells and thymus-derived lymphocites (128). The downstream effect of IL-2 occurs through its high-affinity binding to the receptor IL-2R, consisting of three subunits: IL-2Rα subunit, which is IL-2 specific and IL-2Rβ and IL-2Rγ subunits, which are shared with IL-15. Serum soluble form of IL-2 receptor (siL-2Rα, Tac peptide) is released into circulation by the immune cells. Under physiological conditions its concentration in a blood serum is at a very low level, but it is significantly elevated in some pathologies, for example in the autoimmune diseases, inflammations, some types of leukemia, and allogenic transplant rejections. It has been observed, the level of siL-2Rα correlates with the RA progression, there is also the evidence it induces the expression of IL-15 (Release of sil-2R alpha from and activation of native human peripheral blood mononuclear cells by recombinant IL-15. Treiber-Held S, Stewart D. M, Barraclough H A, Kurman C C, Nelson D L. Clin Immunol Immunopathol. 1996 July; 80(1):67-75).

Currently, different components of the IL-2/IL-2R complex and/or their antagonists, for example, murine monoclonal antibodies (anti-TAC-M) directed toward the human siL-2Rα receptor, are used in the medical treatment. Due to their strong immunogenicity, humanized monoclonal antibodies (anti-TAC-H) recently have been engineered and introduced into clinical practice. Anti-Tac (daclizumab, Zenapax) in the treatment of leukemia, autoimmune diseases, and in the prevention of allograft rejection: a 25-year personal odyssey, Waldmann T A. J Clin Immunol. 2007 January; 27(1): 1-18. The monoclonal antibodies prevent IL-2 binding, among others, to T lymphocytes, thus hampering IL-2 mediated cell response involved in the process of allograft rejection. (WWW.drugbank.ca/drugs/BTD00007).

A need to design a new drug based on a small synthetic molecule has motivated the authors of the present invention to alter the concept of the treatment of the IL-15 overproduction related diseases. This approach relates to the inhibition of the IL-15 biological activity by a compound selectively binding to IL-15Rα receptor. According to the current state of knowledge and our own unpublished results, the strategy, while implemented, should reduce the pro-inflammatory cascade as well as angiogenesis caused by pro-inflammatory cytokine IL-15. The additive synergism may be the most likely explanation of the mechanism, so far unrecognized, of the inhibition of IL-15 biological activity by the biologicals.

The known small chemical molecules of potential application in rheumatoid arthritis, which interfere with the interaction of the receptor IL-15Rα and its ligand (IL-15) are only phenylpyrazole anilide derivatives, disclosed by Ushio H. et al. in Letters in Drug Design Discovery, 5, 292-296 {2008). The molecule Y-320, belonging to the aforementioned group of compounds of proven high bioavailability and in vitro activity, inhibits IL-15-induced T cells activity.

The aim of the present invention was to select a molecule, which would effectively inhibit the biological activity of both IL-15 and IL-2 by selective binding to IL-15 specific IL-15Rα receptor and concomitant blocking IL-2Rβ as well as IL-2Rγ receptor subunits shared by these two cytokines.

The derivatives of 7-aminocephalosporanic acid, cephalosporines, are the group of semi-synthetic β-lactam antibiotics, characterized by broad spectrum of antibacterial activity. The β-lactam antibiotics exert their effect by interfering with the structural crosslinking of peptidoglycans (murein) in bacterial cell walls. They bind covalently to the active sites of D alanyl carboxypeptidase and transpeptidase, inhibiting the activity of these bacterial enzymes involved in the synthesis of bacterial cell wall.

In U.S. Pat. No. 4,891,370 the use of cephalosporanic acid derivatives as anti-inflammatory agents, in particular, of high effectiveness in rheumatoid arthritis, has been disclosed. This anti-inflammatory activity has been attributed to the inhibition of elastase activity by cephalosporins The cephalosporin derivatives, disclosed in U.S. Pat. No. 4,891,370, are substituted at position 3 with the organic radical or the group typical for cephalosporins and penems, while the active hydrogen of the ester group at position 2 of the 6-membered ring is the organic radical.

SUMMARY

The identification of a chemical compound which will fit in the IL-15Rα receptor was facilitated due to the evaluation of the receptor domain structure, which is of key importance while binding to IL-15 (Wei X. et al., J. Immunol. 167, 277-82 (2001)). The search for small chemical molecules fitting in the IL-15 specific receptor domain was carried out on the basis of the model of the [IL-15Rα-IL-15] complex structure, elaborated on the basis of the crystal structure of the complex fragment (2Z3Q code of Protein Data Bank). The assignment of receptor binding sites pharmacophores, while considering specific interactions with IL-15, was enabled due to determination of the 3D structure of the [IL-15Rα-IL-15] complex. It was followed by the search of the small molecules data base ZINC, embracing about 20 million chemical compounds, to find the molecules which can meet the structural requirements for pharmacophores. The screening included more than 10 thousand compounds fulfilling the established criteria. The calculations were also carried out in order to theoretically predict the binding affinity and strength of the selected compounds and the receptor active site. Molecular docking of the chosen molecules was performed using GLIDE software. While docking, the IL-15 binding site of the receptor remained rigid, but the molecule was able to undergo conformational changes due to the modifications of rotating chemical bonds. Additional docking carried out for the pre-selected 500 molecules allowed the induction fitting in of the two interacting partners (protein receptor and small molecule).

Using the above described screening methods, the specific compound has been selected with the efficiency in inhibiting IL-15 and IL-2-induced cell responses in vitro.

The specific compound is 7-aminocephalosporanic acid derivative, known under the International Non-proprietary Name (INN) Cefazolin.

The present invention provides 7-aminocephalosporanic acid derivative-Cefazolin, for use as the inhibitor of IL-15 specific IL-15Rα and IL-2Rβ and IL-2Rγ receptor subunits shared by IL-15 and IL-2, in the prevention and treatment of IL-15 and IL-2 overproduction related diseases.

DESCRIPTION OF THE DRAWINGS

In order to facilitate the present disclosure, reference is made to the following illustrative drawing figures in which like reference numerals are employed where appropriate throughout the various views.

DETAILED DESCRIPTION

Cefazolin is first-generation cephalosporin of broad spectrum of antimicrobial activity. Potent bactericidal activity against Gram-positive bacteria is the reason for the frequent indications of this antibiotic in the clinical practice. The spectrum of Cefazolin antibacterial activity comprises: staphylococci; streptococci, including *Streptococcus pneumoniae* (only penicillin susceptible), *Haemophilus influenzae, Escherichia coli, Proteus mirabilis, Klebsiella pneumoniae*, anaerobic *cocci*.

Cefazolin is most frequently administered in the treatment of serious infections, such as, for example, respiratory tract infection (in particular lower parts of respiratory tract) due to: *S. pneumoniae*, group A β-hemolytic streptococci, *Klebsiella* spp., *H. influenzae, S. aureus*; urinary tract and genital infections due to: *E. coli, P. mirabilis, Klebsiella* spp.; skin and soft tissue infections due to: *S. aureus*, group A β-hemolytic streptococci and the other strains of streptococci; bilary tract infections due to *E. coli* and enterococci, *P. mirabili, Klebsiella* spp. and *S. aureus*; bone and joint infections due to *S. aureus*; septicemia due to *S. pneumoniae, P mirabilis, E. coli, Klebsiella* spp.; endocarditis due to *S. aureus* and group A β-hemolytic streptococci; as well as in perioperative prophylaxis (according to the general indications of the pharmaceutical product).

Cefazolin is very poorly absorbed from gastrointestinal tract, therefore it must be administered parenterally, i.m. or i.v. It has good bioavailability into pleural cavity, peritoneal cavity, synovial fluid, bile, bones, and urinary tract, but it does not cross the blood brain barrier. Cefazolin is not metabolized. It is excreted in urine, due to glomerular filtration mechanism (in a lesser degree by tubular secretion), of unchanged structure at 90% of the excreted amount.

Whenever the term 'Cefazolin' is used hereinafter, it refers to Cefazolin or pharmaceutically acceptable salts thereof, in particular sodium salt.

Cefazolin biological activity with respect to the use according to the invention has been proved in vitro. The studies' results confirm that Cefazolin suppresses IL-15-induced cell proliferation and inhibits IL-15-induced synthesis of TNF-α and IL-17. The same inhibitory activity has been observed when cells were stimulated with IL-2.

These findings indicate Cefazolin may be used to hamper excessive cells' responses induced by IL-15 and IL-2, due to blocking IL-15 specific IL-15Rα receptor and IL-2Rβ and IL-2Rγ receptor subunits, shared by these two cytokines.

In particular, Cefazolin may be used in the prevention and treatment of the diseases from the group comprising rheumatoid arthritis, psoriasis, inflammatory bowel disease, sarcoidosis, T-cell leukemias and transplant rejection.

Preferably, Cefazolin may be used in the treatment of rheumatoid arthritis.

According to the invention, Cefazolin can be administered to an individual in the need of such a treatment, in particular to a human, at therapeutically effective dose.

The term 'treatment' refers to the suppression of a state, a disorder or a disease, which means inhibition, reduction or delay of the disease development, recurrence of the illness or at least one of its symptoms, or recovery, meaning the regression of a state, a disorder or a disease or at least one of its symptoms.

The term 'therapeutically effective dose' refers to the amount of the compound sufficient to produce a therapeutic response when administered to an individual in order to cure a state, a disorder or a disease. The 'therapeutically effective dose' will vary depending on the nature of the selected compound and the route of administration, kind of a disease and its status, age, body weight, physical condition, susceptibility to the treatment, and it can be recommended by a medical doctor on the basis of their own experience and the results of clinical trials.

The therapeutic dose of Cefazolin can be administered as a single dose or divided doses given in certain intervals of time, for example as two, three, four or more daily doses. Maximum daily dose of Cefazolin is 12 g.

The daily dose of Cefazolin in adult may be in the range of 250 to 500 mg or it may be even higher, as administered every 8 or 12 h.

Although the administration of Cefazolin per se may be considered, in general it will be used as active ingredient of the pharmaceutical formulation, of appropriate form suited to the particular route of administration.

Another embodiment of the invention relates to the use of Cefazolin for manufacturing of the pharmaceutical formulation for the prevention or treatment of the diseases such as rheumatoid arthritis, psoriasis, inflammatory bowel disease, sarcoidosis, T-cell leukemias or transplant rejection.

The other embodiment of the present invention relates to the pharmaceutical formulation comprising Cefazolin as the active ingredient and the pharmaceutically acceptable carriers and/or excipients for the prevention or treatment of the diseases such as rheumatoid arthritis, psoriasis, inflammatory bowel disease, sarcoidosis, T-cell leukemias or transplant rejection.

The pharmaceutical formulation-except for the active ingredient—may contain traditional pharmaceutically acceptable carriers and/or excipients which are inert and do not interact with the active ingredient.

The pharmaceutical formulation—except for the active ingredient—may also contain traditional pharmaceutically acceptable carriers and/or excipients which are inert and do not interact with the active ingredient.

The pharmaceutical composition may be formulated in any pharmaceutical form suitable for the systemic administration, for example oral administration, such as tablets and capsules, starch capsules, coated tablets or enteral tablets; as powders or granules; as a solution, a suspension or an emulsion. Tablets and capsules for oral administration may contain excipients routinely used in pharmaceutical practice, such as binders, diluents, disintegrants or lubricants. The tablets may be coated by any method known in the art. Liquid pharmaceutical compositions for oral administration may be manufactured as, for example, aqueous or oily suspensions, solutions, emulsions, syrups and elixirs or they may be produced as dry substances for the preparation of solutions or suspensions ex tempore with water or other suitable diluent. Liquid pharmaceutical preparations may contain excipients routinely used in pharmaceutical practice, such as dispersing and emulsifying agents, non-aqueous carriers (they may comprise eatable oils) or preservatives. The selection and amount of the excipients depends on the pharmaceutical dosage form and the route of drug administration. The pharmaceutical composition may be formulated into any suitable pharmaceutical form, by any method known in the art, using any pharmaceutically acceptable carriers, diluents, fillers and other excipients.

On account of very poor absorption when Cefazolin is administered orally, parenteral, i.e. intra-venous or intra-muscular route of administration is preferred. The pharmaceutical preparation suitable for parenteral administration, for example for intramuscular, subcutaneous or intravenous administration, may be used as a ready suspension, lyophilizate, suspension ex tempore or concentrate for intravenous infusions. These preparations may be formulated as unit dosage forms in ampoules, initially filled syringes, low capacity infusions, or in multi-dosage containers consisting of preservatives and carriers, diluents, stabilizers and/or dispersing agents. The carriers suitable for the intravenous administration of the pharmaceutical preparation comprise, for example, sterile aqueous solutions, such as the solution of physiological salt, the solutions of carbohydrates, for example, glucose, mannitol, dextrose, lactose and aqueous buffer solutions, for example, phosphate buffers. The pharmaceutical composition may also contain other excipients routinely used to maintain isoosmoticity, antioxidants, preservatives and others. Alternatively, the active ingredient may be used as the powder obtained due to isolation of a solid compound under septic conditions or by lyophilisation from the solvent, for the preparation of suspensions ex tempore in a suitable diluent, for example, sterile water deprived of pyrogenic substances. The substance for intravenous infusions prepared analogously as for the intravenous injections, can be diluted with glucose or Ringer solution or with aqueous 0.9% sodium chloride and as such can be delivered into the body through a vain.

The biological activity of Cefazolin, inhibiting IL-15 and IL-2-induced cells' response has been proved during in vitro studies. The results also demonstrated inhibition of cell proliferation as well as the synthesis of TNF-α and IL-17, induced by these two cytokines. When this effectiveness is proved in vivo studies in animal model of the diseases, Cefazolin will have the potential to be used in the prevention and treatment of IL-15 overproduction-related diseases and inflammations, such as rheumatoid arthritis, psoriasis, inflammatory bowel disease, sarcoidosis, T-cell leukemias or transplant rejection.

Biological Studies

In Vitro Studies

All experiments were carried out on peripheral blood mononuclear cells (PBMC) from healthy donors. The cells were isolated under the standard protocol regarding density gradient centrifugation. According to the general protocol, 6 ml of blood was layered on 3 ml of Lymphoprep (Axis-shield, Norway), then centrifuged at 800×g for 15 min. The layer of PBMC was collected, the cells were washed twice with phosphate buffered saline (PBS) (BIOMED-LUBLIN, Poland) and suspended in medium RPMI1640 (Gibco, Great Britain), containing 10 mM HEPES (Sigma, USA), 10% fetal calf serum (BIOMED-LUBLIN, Poland) and antibiotic (streptomycin sulfate, penicillin G sodium; amphotericin B, PAA, Austria).

Cefazolin was initially selected at the screening stage, on the basis of the three-dimensional structure of the model of [IL-15Rαβγ-IL-15] protein complex. Cefazolin was used as sodium salt, commercially available as lyophilizate for preparation of suspensions for the injections (Biofazolin, by ZF Polpharma SA).

The study regarding the assessment of Cefazolin efficacy was performed.

In all the in vitro experiments non-stimulated PBMC were used as the control. The inhibition efficacy was assessed in relation to the cells stimulated with IL-15 or IL-2.

Example I

Effect of Cefazolin on Interleukin 15 or Interleukin 2-Induced PBMC Proliferation.

PBMC proliferation was evaluated using commercially available BrdU Cell Proliferation Assay (Calbiochem, Merck, Germany). PBMC were seeded in a 96-well plate ($25\times10^3$ cells in 200 μL of the culture medium/well). The next day the cells were treated with the tested compound at final concentrations: 20 μM, 100 μM and 300 μM. After 30 min. incubation with Cefazolin, cells were stimulated with IL-15 at the final concentration 5 ng/ml or 11-2 at the final concentration 5 ng/ml. Cells were incubated for 4 days, then for last 24 h bromodeoxyuridine (BrdU) was added to the culture medium at the concentration recommended by the manufacturer. After the completion of the incubation, cells were centrifuged (10 min., 160×g) and fixed. Further experimental steps were performed according to the manufacturer's protocol.

Figure 1:
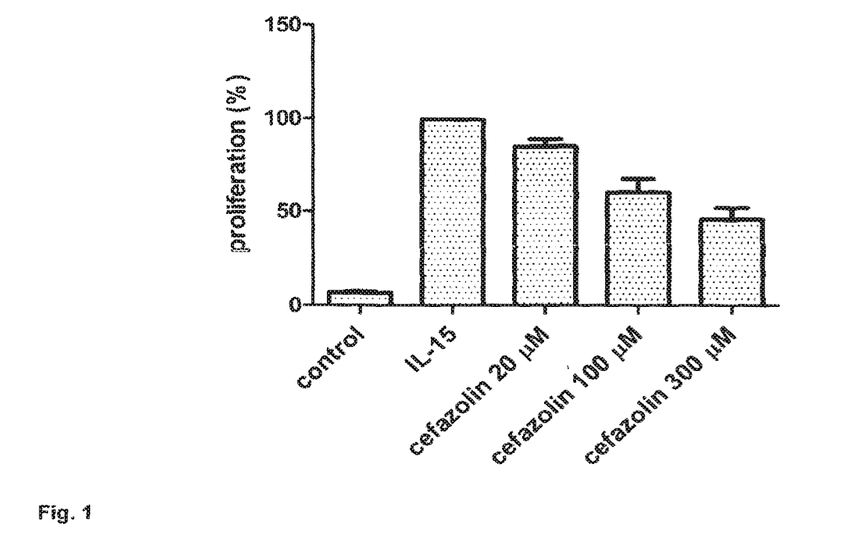
FIG. 1 shows the effect of Cefazolin at different concentration on proliferation of IL-15-stimulated PBMC.
Figure 2:
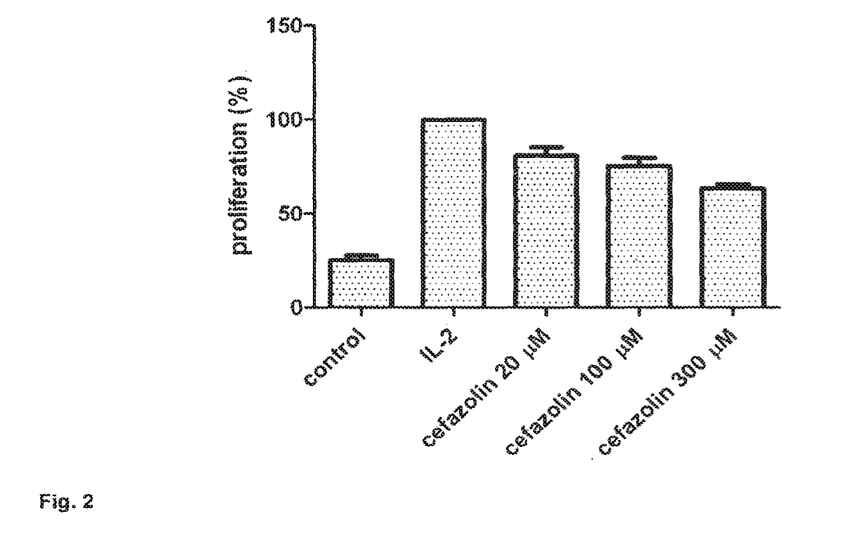
FIG. 2 shows the effect of Cefazolin at different concentration on proliferation of IL-2-stimulated PBMC.

The results of the effect of Cefazolin at different concentrations on IL-15 or IL-2-induced PBMC proliferation are presented in FIG. 1 and FIG. 2 respectively. The results are expressed as the percentage change of proliferating cells with regard to the control cells stimulated with IL-15 or IL-2.

Example II

Effect of Cefazolin on Il-15 or Il-2-Induced TNF-α Synthesis in PBMC.

The evaluation of TNF-α synthesis in IL-15-stimulated PBMC was performed using the ELISA method and commercially available tests (R&D, USA). The experiment was carried out strictly according to the manufacturer's recommendations.

The PBMC were seeded in a 24-well plate ($2\times10_6$ cells in 1 ml of the culture medium/well), treated with the tested compound and after 30 min stimulated with IL-15 (5 ng/ml) or IL-2 (5 ng/ml). After 48 h incubation, the culture medium was collected from each well to determine the TNF-α concentration, cells were harvested and lysed, and the concentration of total protein was measured in cell lysates. The obtained values of TNF-α concentration were calculated for 1 mg of protein. The results are expressed as the percentage change of the concentration of TNF-α synthesized in PBMC with regard to the control cells stimulated with IL-15.

Figure 3:
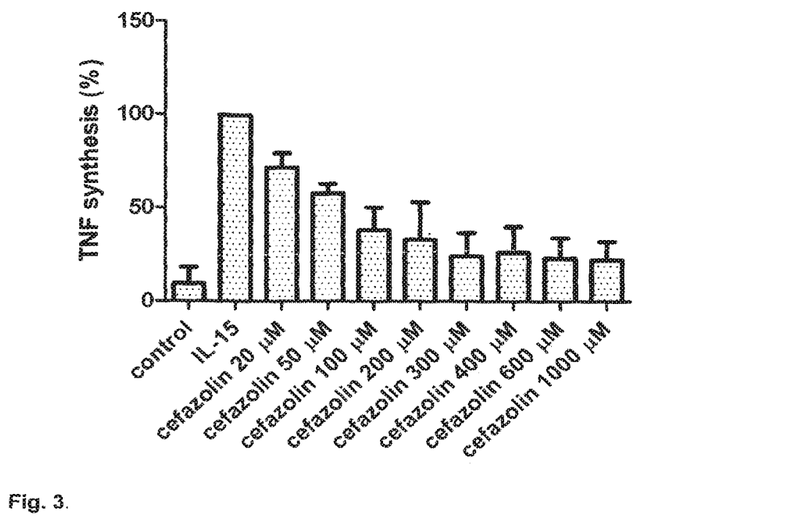
FIG. 3 shows the effect of Cefazolin on IL-15-induced TNF-α synthesis in PBMC.
Figure 4:
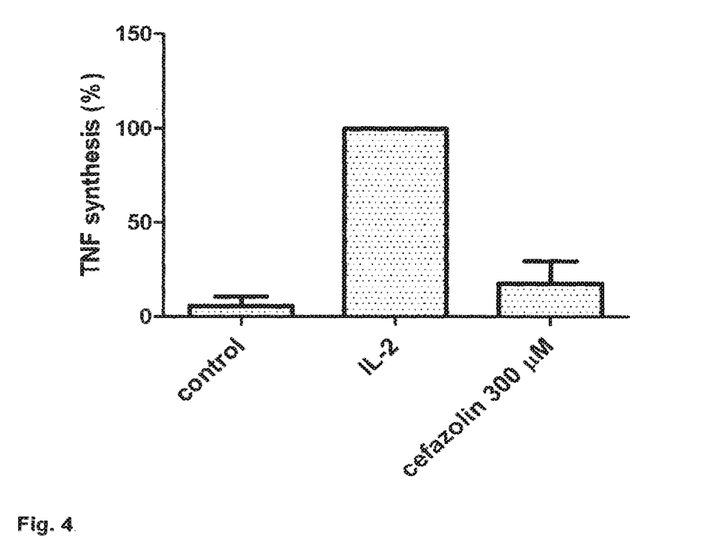
FIG. 4 shows the effect of Cefazolin on IL-2-induced TNF-α synthesis in PBMC.

The effect of Cefazolin at different concentrations (20 μM, 50 μM, 100 μM. 200 μM, 400 μM, 600 μM, 1000 μM) on IL-15-induced TNF-α synthesis in PBMC is depicted in FIG. 3. The effect of Cefazolin at 300 μM concentration on IL-2-induced TNF-α synthesis in PBMC is depicted in FIG. 4.

Cefazolin significantly reduces IL-15 or IL-2-induced TNF-α synthesis in PBMC in comparison with IL-15 and IL-2 stimulated control cells.

Example III

Effect of Cefazolin on IL-15 or IL-2-Induced IL-17 Synthesis in PBMC.

The evaluation of IL-17 synthesis in IL-15- or IL-2-stimulated PBMC was performed using the ELISA method and commercially available tests (R&D, USA). The experiment was carried out strictly according to the manufacturer's recommendations.

PBMC were seeded in a 24-well plate ($2\times10_6$ cells in 1 ml of the culture medium/well), treated with the inhibitor, after 30 min. stimulated with IL-15 (5 ng/ml) or IL-2 (5 ng/ml). After 48 hr incubation, the culture medium was collected from each well to determine the IL-17 concentration, cells were harvested and lysed, and the concentration of total protein was measured in cell lysates. The obtained values of IL-17 concentration were calculated for 1 mg of protein. The results are expressed as the percentage change of the concentration of IL-17 synthesized in PBMC with regard to the control cells stimulated with IL-15 or IL-2.

Figure 5:
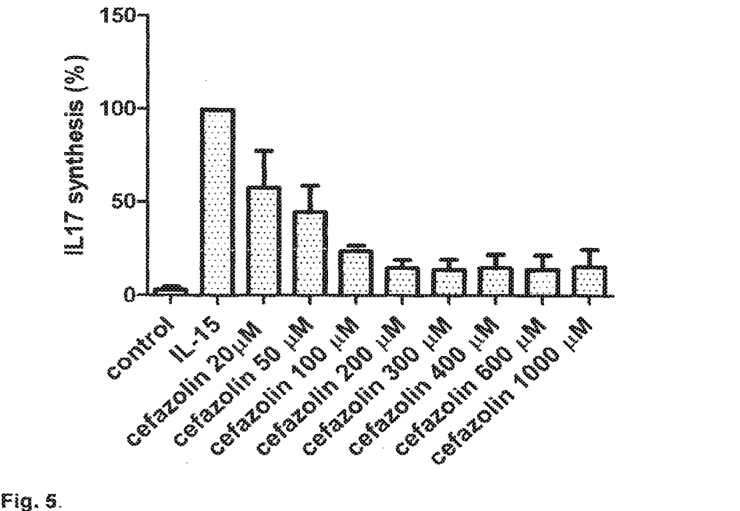
FIG. 5 shows the effect of Cefazolin on IL-15-induced IL-17 synthesis in PBMC.
Figure 6:
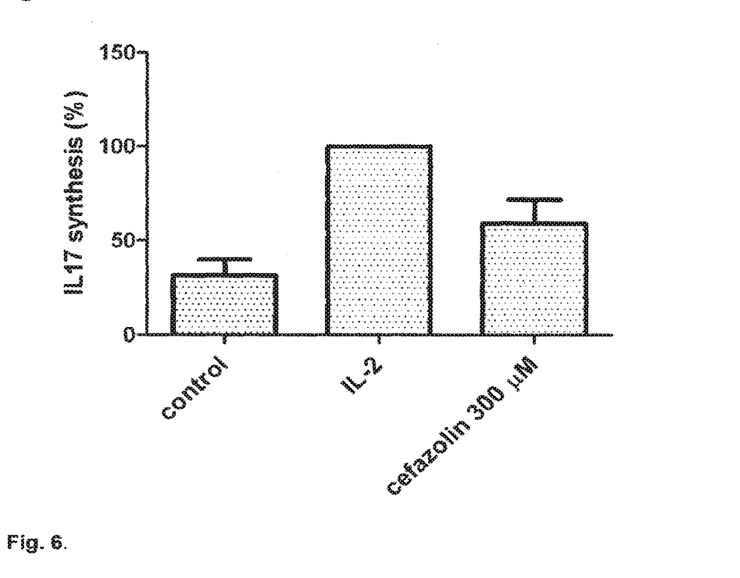
FIG. 6 shows the effect of Cefazolin on IL-2-induced IL-17 synthesis in PBMC.

The effect of Cefazolin at different concentrations (20 μM, 50 μM, 100 μM, 200 μM, 300 μM, 400 μM, 600 μM and 1000 μM) on IL-15-induced IL-17 synthesis in PBMC is depicted in FIG. 5. The effect of Cefazolin at 300 μM concentration on IL-2-induced IL-17 synthesis in PBMC is depicted in FIG. 6.

Cefazolin significantly reduces IL-15-induced IL-17 synthesis in PBMC in comparison with IL-15 stimulated control cells. The increase of Cefazolin concentration from 200 μM to 1000 μM does not affect IL-17 synthesis to any great extent. Strong inhibitory effect of Cefazolin on IL-17 synthesis is observed in cells stimulated with IL-2.

Discussion

1. Initial studies based on the assessment of Cefazolin cytotoxicity and efficacy of inhibition of IL-15 or IL-2-induced cell proliferation.

Increased cell proliferation is one of the characteristic responses to IL-15 or IL-2 stimulation. Selective blocking of the IL-15 specific IL-15Rα receptor as well as shared by IL-15 and IL-2, IL-2Rβ and IL-2Rγ the receptor subunits, results in the inhibition of the biological activity of the said cytokines. As a consequence, IL-15 or IL-2-induced increase of cell proliferation does not occur. The effect of Cefazolin on the proliferation of peripheral blood mononuclear cells (PBMC) isolated from blood of healthy donors was evaluated in the assay using a fluorescent CSFE dye (Molecular Dynamics, Great Britain) and in the bromodeoxyuridine incorporation test (BrdU) (BrdU Cell Proliferation Assay, Calbiochem, USA). The PBMC population consists of several cell types, among others, there are lymphocytes and monocytes. Due to expression of IL-15 and IL-2 receptors on the surface of the membrane, extensive proliferation of these cells occurs in response to interleukin 15 or interleukin 2 stimulation. The inhibition of cell proliferation in the presence of the tested compound can be a visible sign of cells' death caused by the cytotoxic or apoptotic activity of the analyzed compound. The effect of Cefazolin on cells viability was tested measuring the lactate dehydrogenase (LDH) concentration in the culture medium and cultured cells (CytoTox 96 Non-Radioactive Cytotoxicity Assay, Promega, USA). LDH is a cytosolic enzyme which under physiological conditions is not released from cells. However, when cell membrane damage or cell death occurs, LDH enzyme is released into the matrix. Increased LDH activity in the culture medium correlates with the increased number of dead cells resulting from the cytotoxic effect of the tested compound. LDH activity measured in cell lysates is used for the assessment of a number of living cells. The results of the following study has demonstrated biological activity of Cefazolin, which inhibits IL-15- or IL-2-induced PBMC proliferation and does not trigger the apoptotic pathway. The experiments were repeated three time on PBMC from different donors.

2. The Assessment of Inhibitory Effectiveness of Cefazolin on IL-15 and IL-2-Induced TNF-α and IL-17 Syntheses.

Peripheral blood mononuclear cells (PBMC) respond to IL-15 or IL-2 stimulation not only by increased proliferation, but also synthesizing many pro-inflammatory cytokines, among others, for example, TNF-α and IL-17. The inhibition of IL-15 and IL-2 biological activity should result in the reduced cell proliferation and decreased syntheses of TNF-α and IL-17.

Cefazolin at different concentrations was used to assess its effect on IL-15 and IL-2-induced other cytokines syntheses. The biological activity of Cefazolin was evaluated measuring the TNF-α and IL-17 concentrations in the culture media collected after the completion of the incubation, using the immunoenzymatic ELISA tests.

The tests results prove the inhibition of the TNF-α and IL-17 syntheses and they serve as the following evidence of Cefazolin biological activity.

While the invention has been described in connection with what is presently considered to be the most practical and preferred embodiment, it is to be understood that the invention is not to be limited to the disclosed embodiments but, on the contrary, is intended to cover various modifications and equivalent arrangements included within the spirit and scope of the appended claims, which scope is to be accorded the broadest interpretation so as to encompass all such modifications and equivalent structures as is permitted under the law.

What is claimed:

1. A method of treating psoriasis in a patient comprising:
   (1) a step of identifying a patient having elevated levels of one or more selected from the group consisting of IL-2, IL-15, IL-17, and TNF-α; and
   (2) a step of treating the patient by administering to the patient in need thereof a therapeutically effective dose Cefazolin or pharmaceutically acceptable salts thereof or pharmaceutically acceptable composition thereof wherein the pharmaceutically acceptable compositions comprise a therapeutically effective dose of Cefazolin or pharmaceutically acceptable salts thereof and a pharmaceutically acceptable excipient, carrier or diluent.

2. The method according to claim 1, wherein the pharmaceutically acceptable compositions are administered intravenously or intramuscularly.

3. The method of claim 1 wherein the therapeutically effective dose of Cefazolin administered is sufficient to provide a serum concentration between 20 μm and 300 μm.

4. The method of claim 1 wherein the therapeutically effective dose of Cefazolin initially administered is between 250 and 500 mg followed by administration of a therapeutically effective dose between 250 and 500 mg of Cefazolin after an interval of between 8 to 12 hours.

5. The method of claim 1, wherein the method comprises either:
   i) administering to the patient in need thereof the therapeutically effective dose of Cefazolin or pharmaceutically acceptable salts thereof, wherein the Cefazolin or pharmaceutically acceptable salts thereof is the sole active ingredient, or
   ii) administering to the patient in need thereof the pharmaceutically acceptable composition, wherein the Cefazolin or pharmaceutically acceptable salts thereof is the sole active ingredient.

6. A method of reducing the amount of IL-15 and/or IL-2 in a patient having psoriasis comprising:
   (1) a step of identifying a patient having elevated levels of one or more selected from the group consisting of IL-2 and IL-15: and
   (2) a step of treating the patient by administering to the patient in need thereof a therapeutically effective dose of Cefazolin or pharmaceutically acceptable salts thereof or pharmaceutically acceptable compositions thereof wherein the pharmaceutically acceptable compositions comprise a therapeutically effective dose of Cefazolin or pharmaceutically acceptable salts thereof and a pharmaceutically acceptable excipient, carrier or diluent.

7. The method of claim 6 wherein the therapeutically effective dose of Cefazolin is administered intravenously or intramuscularly.

8. The method of claim 6 wherein the therapeutically effective dose of Cefazolin administered is sufficient to provide a serum concentration between 20 μM and 300 μM.

9. The method of claim 6, wherein the method comprises either:
   i) administering to the patient in need thereof the therapeutically effective dose of Cefazolin or pharmaceutically acceptable salts thereof, wherein the Cefazolin or pharmaceutically acceptable salts thereof is the sole active ingredient, or
   ii) administering to the patient in need thereof the pharmaceutically acceptable composition, wherein the Cefazolin or pharmaceutically acceptable salts thereof is the sole active ingredient.

10. A method for reducing synthesis of TNF-α and/or IL-17 in a patient having psoriasis comprising:
    (1) a step of identifying a patient having elevated levels of one or more selected from the group consisting of IL-17 and TNF-α; and
    (2) a step of treating the patient by parenterally administering to the patient in need thereof a therapeutically effective dose of Cefazolin or pharmaceutically acceptable salts thereof or pharmaceutically acceptable compositions thereof wherein the pharmaceutically acceptable compositions comprise a therapeutically effective dose of Cefazolin or pharmaceutically acceptable salts thereof and a pharmaceutically acceptable excipient, carrier or diluent.

11. The method of claim 10, wherein the method comprises either:
    i) administering to the patient in need thereof the therapeutically effective dose of Cefazolin or pharmaceutically acceptable salts thereof, wherein the Cefazolin or pharmaceutically acceptable salts thereof is the sole active ingredient, or
    ii) administering to the patient in need thereof the pharmaceutically acceptable composition, wherein the Cefazolin or pharmaceutically acceptable salts thereof is the sole active ingredient.

12. A method for preventing overproduction of IL-15 and/or IL-2 in a patient having psoriasis comprising:
    (1) a step of identifying a patient having psoriasis associated with overproduction of one or more selected from the group consisting of IL-2 and IL-15; and
    (2) a step of treating the patient by administering to the patient in need thereof a therapeutically effective dose of Cefazolin or pharmaceutically acceptable salts thereof or pharmaceutically acceptable compositions thereof wherein the pharmaceutically acceptable compositions comprise a therapeutically effective dose of Cefazolin or pharmaceutically acceptable salts thereof and a pharmaceutically acceptable excipient, carrier or diluent.

13. The method of claim 12, wherein the method comprises either:
  i) administering to the patient in need thereof the therapeutically effective dose of Cefazolin or pharmaceutically acceptable salts thereof, wherein the Cefazolin or pharmaceutically acceptable salts thereof is the sole active ingredient, or
  ii) administering to the patient in need thereof the pharmaceutically acceptable composition, wherein the Cefazolin or pharmaceutically acceptable salts thereof is the sole active ingredient.

* * * * *